(12) United States Patent
Vrabec et al.

(10) Patent No.: US 11,628,299 B2
(45) Date of Patent: Apr. 18, 2023

(54) SUBCUTANEOUS DIRECT CURRENT NERVE CONDUCTION BLOCK

(71) Applicant: Case Western Reserve University, Cleveland, OH (US)

(72) Inventors: Tina Vrabec, Cleveland, OH (US); Niloy Bhadra, Cleveland, OH (US); Narendra Bhadra, Cleveland, OH (US); Kevin L. Kilgore, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 316 days.

(21) Appl. No.: 16/341,511

(22) PCT Filed: Oct. 17, 2017

(86) PCT No.: PCT/US2017/056911
§ 371 (c)(1),
(2) Date: Apr. 12, 2019

(87) PCT Pub. No.: WO2018/075473
PCT Pub. Date: Apr. 26, 2018

(65) Prior Publication Data
US 2020/0001078 A1 Jan. 2, 2020

Related U.S. Application Data

(60) Provisional application No. 62/408,864, filed on Oct. 17, 2016.

(51) Int. Cl.
*A61N 1/36* (2006.01)
*A61N 1/05* (2006.01)
*A61N 1/18* (2006.01)

(52) U.S. Cl.
CPC ....... *A61N 1/36007* (2013.01); *A61N 1/0504* (2013.01); *A61N 1/0551* (2013.01); *A61N 1/18* (2013.01); *A61N 1/36075* (2013.01)

(58) Field of Classification Search
CPC .............. A61N 1/36007; A61N 1/0504; A61N 1/0551; A61N 1/18; A61N 1/36075; A61N 1/36021; A61N 1/36017; A61N 1/3605
See application file for complete search history.

(56) References Cited

U.S. PATENT DOCUMENTS

| 7,203,548 | B2 * | 4/2007 | Whitehurst | A61N 1/0556 607/118 |
| 7,373,204 | B2 * | 5/2008 | Gelfand | A61N 1/36114 607/44 |

(Continued)

FOREIGN PATENT DOCUMENTS

| WO | 2009/158389 A1 | 12/2009 |
| WO | 2016/032929 A2 | 3/2016 |

OTHER PUBLICATIONS

Amatya, Bhasker, et al. "Non pharmacological interventions for spasticity in multiple sclerosis." Cochrane database of systematic reviews 2 (2013).

(Continued)

*Primary Examiner* — Mark W. Bockelman
(74) *Attorney, Agent, or Firm* — Tarolli, Sundheim, Covell & Tummino LLP (57) ABSTRACT

The present disclosure relates to subcutaneous direct current (DC) nerve conduction block. A subcutaneous electrode can be implanted under a subject's skin between the subject's skin and a neural structure within the subject's body. The subcutaneous electrode can be coupled to a current generator. A DC can be configured by the current generator and delivered through the subcutaneous electrode to block con- (Continued)

duction in the neural structure. The subcutaneous electrode eliminates an effect of an impedance of the subject's skin on the DC. The DC can be returned to the current generator by a return electrode.

14 Claims, 5 Drawing Sheets

(56) References Cited

U.S. PATENT DOCUMENTS

| | | | |
|---|---|---|---|
| 8,983,614 B2* | 3/2015 | Kilgore | A61N 1/32 607/48 |
| 2010/0016929 A1 | 1/2010 | Prochazka | |

OTHER PUBLICATIONS

Baron, Ralf. "Neuropathic pain: a clinical perspective." Sensory Nerves. Springer, Berlin, Heidelberg, 2009. 3-30.
Dormandy, John, Ludger Heeck, and Stella Vig. "Major amputations: clinical patterns and predictors." Seminars in vascular surgery. vol. 12. No. 2. 1999.
Franke, Manfred, et al. "Chronic bladder control post SCI via Electric Pudendal Nerve Block."
Franke, M., N. Bhadra, and K. J. Gustafson. "Chronic bladder voiding after SCI using electric HFAC pudendal nerve block." Neural Interfaces Conference. 2012.
Kilgore, Kevin L., and Niloy Bhadra. "Reversible nerve conduction block using kilohertz frequency alternating current." Neuromodulation: Technology at the Neural Interface 17.3 (2014): 242-255.
Koch, Horst, et al. "Treatment of painful neuroma by resection and nerve stump transplantation into a vein." Annals of plastic surgery 51.1 (2003): 45-50.
Lin, Yin-Tsong, et al. "Dual-channel neuromodulation of pudendal nerve with closed-loop control strategy to improve bladder functions." J Med Biol Eng 34.34 (2014): 82-9.
Lundstrom, Erik, et al. "Four-fold increase in direct costs of sloke survivors with spasticity compared with stroke survivors without spasticity: the first year after the event." Stroke 41.2 (2010): 319-324.
Naples, Gregory G., et al. "A spiral nerve cuff electrode for peripheral nerve stimulation." IEEE transactions on biomedical engineering 35.11 (1988): 905-916.
Rizzo, M. A., et al. "Prevalence and treatment of spasticity reported by multiple sclerosis patients." Multiple Sclerosis Journal 10.5 (2004): 589-595.
PCT International Search Report and Written Opinion for corresponding PCT Application Serial No. PCT/US2017/056911, dated Jan. 24, 2018, pp. 1-13.
Stokvis, Annemieke, J. Henk Coert, and Johan W. van Neck. "Insufficient pain relief after surgical neuroma treatment: prognostic factors and central sensitisation." Journal of plastic, reconstructive & aesthetic surgery 63.9 (2010): 1538-1543.
Tiede, Jeffrey, et al. "Novel spinal cord stimulation parameters in patients with predominant back pain." Neuromodulation: Technology at the Neural Interface 16.4 (2013): 370-375.

* cited by examiner

SUBCUTANEOUS DIRECT CURRENT NERVE CONDUCTION BLOCK

RELATED APPLICATION

This application claims priority to U.S. Provisional Application Ser. No. 62/408,864, filed Oct. 17, 2016, entitled "SUBCUTANEOUS DC NERVE CONDUCTION BLOCK", the entirety of which is hereby incorporated by reference for all purposes.

TECHNICAL FIELD

The present disclosure relates generally to subcutaneous direct current (DC) nerve conduction block and, more specifically, to systems and methods using an arrangement of subcutaneous electrodes to deliver the DC nerve conduction block to alter conduction in a neural structure.

BACKGROUND

Many neurological disorders are characterized by unwanted neural activity, which induces pathological effects at the end organs. The unwanted neural activity can be reduced due to an electrical block of action potential conduction in the nerve causing the unwanted neural activity. The electrical block can be due to the application of a depolarizing or hyperpolarizing electrical field. The electric field can be caused by a kilohertz frequency alternating current (KHFAC) block, which produces a steady state depolarization, or a direct current (DC) block, which produces either a depolarization or hyperpolarization depending on the polarity of the signal. If the electrical field is applied too quickly, nerve fibers can experience an onset response due to spurious firing. With DC block, the onset response can be mitigated simply by ramping the field up to the block threshold over time. However, the onset block cannot be eliminated with KHFAC block due to variations in the high frequency component. Therefore, DC block is generally preferable to KHFAC block.

The lowest electrical field that results in a functional block of fibers in the nerve is referred to as the "block threshold". Due to their size, motor fibers are blocked with lower block thresholds than smaller fibers, such as pain fibers or autonomic fibers. Generally, a nerve cuff can place cuff electrodes directly on the nerve, producing the most concentrated electrical field on the nerve, resulting in the lowest possible block thresholds and the shortest ramp time to prevent the onset response. The use of a nerve cuff also minimizes the spread of the signal into the surrounding tissue, reducing the possibility that other nerves will be blocked. However, nerve cuff electrodes are, by definition, highly invasive. A less invasive solution to achieve the nerve block is desirable for many applications. While it is possible to generate nerve block using surface electrodes, the impedance of the skin to electrode interface causes the block threshold to be particularly high, reducing the utility of such surface electrodes.

SUMMARY

Subcutaneous electrodes, which are placed under the skin, near the nerve, but not on the nerve, eliminate the high impedance of the skin to electrode interface. Accordingly, the present disclosure relates generally to subcutaneous direct current (DC) nerve conduction block and, more specifically, to systems and methods using an arrangement of subcutaneous electrodes to deliver the DC nerve conduction block to alter conduction in a neural structure.

In another aspect, the present disclosure can include a system that can use an arrangement of subcutaneous electrodes to deliver the DC nerve conduction block to alter conduction in a nerve. The system can include a current generator that generates a DC. The current generator can be coupled to a subcutaneous electrode to deliver the DC to block conduction in conduction in one or more neural structures in the subject's body. The subcutaneous electrode is implantable under the subject's skin and between the subject's skin and a neural structure within the subject's body to eliminate an effect of an impedance of the subject's skin on the DC. The system can also include a return electrode, also coupled to the current generator, to return the DC to the current generator.

In a further aspect, the present disclosure can include a method using an arrangement of subcutaneous electrodes to deliver the DC nerve conduction block to alter conduction in one or more neural structure in a subject's body. A subcutaneous electrode can be implanted under the subject's skin between the subject's skin and a neural structure within the subject's body. The subcutaneous electrode can be coupled to a current generator. A DC can be configured by the current generator and delivered through the subcutaneous electrode to block conduction in the neural structure. The subcutaneous electrode eliminates an effect of an impedance of the subject's skin on the DC. The DC can be returned to the current generator by a return electrode.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "electric field" can refer to a region around a charged particle or object within which a force would be exerted on other charged particles or objects. The electric field can be defined as the electric force per unit charge.

As used herein, the term "electrical block" can refer to the attenuation of conduction in at least one nerve fiber due to a change in the electric field caused by application of an electrical signal to the nerve. The terms "electrical block" and "nerve conduction block" can be used interchangeably herein.

As used herein, the term "electrical signal" can refer to a function that conveys information about the behavior or attributes of an electric phenomenon, such as electric current, that varies with time and/or space. For example, the electrical signal can be an alternating current (e.g., kilohertz frequency alternating current) signal and/or a direct current signal.

As used herein, the terms "direct current" or "DC" can refer to a unidirectional flow of electric charge. In some instances, the DC can have a plateau of a cathodic polarity or an anodic polarity. The DC can further be represented as a waveform that includes a ramp from a zero position to the plateau. In some instances, the waveform can also include a ramp down from the plateau position to the zero position. In still other instances, the waveform can include a subsequent plateau of the opposite polarity (in such cases, the waveform can be a biphasic waveform with the second phase configured to reduce charge either as a charge balanced waveform or a charge imbalanced waveform). The waveform can also include ramps from zero to the plateau and/or from the plateau to zero.

As used herein, the term "direct current block" or "DC block" can refer to the application of a direct current pulse with a polarity configured depolarization or hyperpolarization to cause change in the electric field sufficient to alter conduction in the nerve.

As used herein, the term "block threshold" can refer to the lowest magnitude change in electrical field that results in a functional block of one or more nerve fibers suitable for an application.

As used herein, the term "onset response" can refer to transient neural activity that occurs for a time when an electrical block is applied. With a DC block, the onset response can be mitigated by ramping the field up to the block threshold over time.

As used herein, the terms "alter" or "altering", when used with reference to nerve conduction, can refer to affecting or changing a manner in which action potentials are conducted in a nerve. In some instances, nerve conduction can be altered by extinguishing an action potential at some point as it travels along the nerve (also referred to as "blocking" nerve conduction). In other instances, nerve conduction can be altered by increasing the activation threshold of a nerve and/or decreasing the conduction velocity of a nerve (also referred to as "attenuating" nerve conduction).

As used herein, the term "neural structure" can refer to tissue related to the central nervous system, peripheral nervous system, autonomic nervous system, and enteric nervous system. The term neural structure, in some instances, can include one or more nerves and/or neural fibers.

As used herein, the term "nerve" can refer to one or more fibers that employ electrical and chemical signals to transmit information. A nerve can refer to either a component of the central nervous system or the peripheral nervous system. For example, in the peripheral nervous system a nerve can transmit motor, sensory, autonomic, and/or enteric information from one body part to another As used herein, the term "fiber" can refer to an axon of a neuron.

As used herein, the term "neurological disorder" can refer to a condition or disease characterized at least in part by abnormal conduction in one or more nerves. The neurological disorder can be in the motor system, the sensory system, and/or the autonomic system.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

As used herein, the term "medical professional" can refer to an individual who provides care to a patient. A medical professional can be, for example, a doctor, a physician's assistant, a student, a nurse, a caregiver, or the like.

II. Overview

The present disclosure is directed to nerve conduction block due to application of an electrical field to a neural structure. Application of a direct current (DC) to the neural structure can provide either a depolarizing or hyperpolarizing electric field. Additionally, the DC can be configured to ramp the field up to the block threshold over time to mitigate an onset response of the neural structure. Therefore, DC is desirable over traditional alternating current (such as kilohertz frequency alternating current) for application of the electric field to the neural structure for nerve conduction block applications. Traditionally, the electrical field has been generated by placing cuff electrodes directly on the neural structure. Use of such cuff electrodes provides the most concentrated electrical field on the neural structure, resulting in the lowest possible block thresholds and a short ramp to the block threshold. Additionally, use of cuff electrodes minimizes the spread of the applied current to the surrounding tissue, reducing the possibility that other neural structures will be affected. However, the invasive nature of these cuff electrodes makes use of the cuff electrodes impractical for use many clinical and experimental applications.

Many of these clinical and experimental applications would benefit from a less invasive alternative for generation of DC nerve block. Using surface electrodes, the least invasive solution, it is possible to generate a DC nerve block. However, the DC applied via surface electrodes is subject to the impedance of the skin to electrode interface, causing the block threshold to be particularly high. The block threshold can be reduced by using subcutaneous electrodes, which are placed under the skin, but need not be placed directly in contact with the neural structure. Accordingly, the present disclosure relates generally to subcutaneous direct current (DC) nerve conduction block and, more specifically, to systems and methods using an arrangement of subcutaneous electrodes to deliver the DC nerve conduction block. The subcutaneous electrode configuration vastly improves the impedance of the electrode, allowing the achievement of lower block thresholds and providing a more localized field than surface electrodes, while still being less invasive than cuff electrodes, which is advantageous for many clinical and experimental applications.

III. Systems

One aspect of the present disclosure can include a system 10 (FIG. 1) that can deliver a direct current (DC) nerve conduction block to one or more neural structures subcutaneously. The subcutaneous application of the DC nerve conduction block can provide a minimally invasive solution (that is less invasive than cuff electrodes), while removing the impedance that hampers the DC block (removing the skin to electrode interface impedance inherent to surface electrodes). For example, the impedance can be at least 50% lower with a subcutaneous electrode compared to a surface electrode of similar size and material, which translates directly into the less current/charge required to achieve DC nerve conduction block. As another example, the impedance can be at least 60% lower with a subcutaneous electrode compared to a surface electrode of similar size and material. In a further example, the impedance can be at least 70% lower with a subcutaneous electrode compared to a surface electrode of similar size and material. By removing the skin to electrode interface impedance, subcutaneous DC nerve conduction block can achieve lower block thresholds, which can, for example, be easier to mitigate the onset response using a ramped signal. Additionally, when the DC nerve conduction block is delivered simultaneously, the position under the skin can provide a more localized field and prevent the spreading of the electrical field to other neural structures.

In one example, the neural structure can be a peripheral nerve (e.g., motor, sensory, and/or autonomic/enteric) or a nerve or nervous tissue comprising the central nervous system (e.g., brain and/or spinal cord). The DC nerve conduction block can be used to treat various neurological disorders including, but not limited to, chronic neuropathic pain or muscle spasticity. The DC nerve conduction block can also be used to modulate or inhibit neural activity in the autonomic or enteric system. Additionally, the DC nerve conduction block can be used to manage regional applications, like chronic headache management or bladder control.

Figure 1:
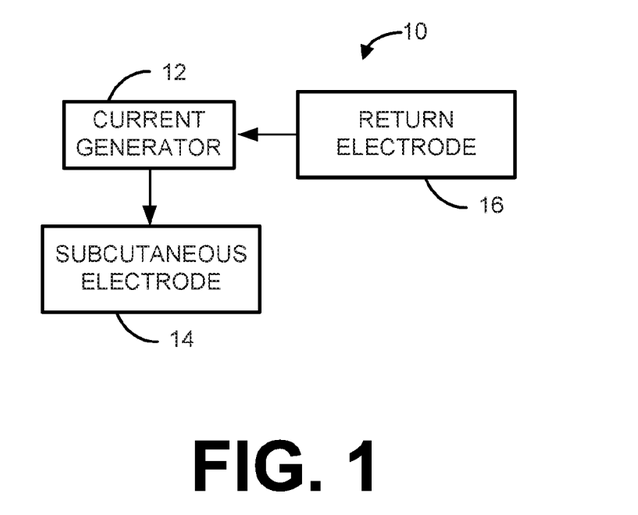
FIG. 1 is a diagram showing a system that can use an arrangement of subcutaneous electrodes to deliver a direct current (DC) nerve conduction block in accordance with an aspect of the present disclosure.

The system 10 can include a current generator 12, which is coupled to a subcutaneous electrode 14 and a return electrode 16. In some instances, the coupling of the current generator 12 to each of the subcutaneous electrode 14 and the return electrode 16 can be via a wired connection (e.g., via a percutaneous wire or a subcutaneous wire). In other instances, the coupling of the current generator 12 to each of the subcutaneous electrode 14 and the return electrode 16 can be via a wireless connection. In still other instances, the coupling of the current generator 12 to each of the subcutaneous electrode 14 and the return electrode 16 can be via a connection that is both wired and wireless.

The current generator 12 can be configured or programmed to generate a DC of sufficient amplitude to cause the DC nerve conduction block in a target neural structure. Accordingly, the current generator 12 can be any device configured or programmed to generate the specified DC current for application to the target neural tissue to achieve an alternation in conduction thereof. One example of a current generator 12 is a battery-powered, portable generator (the current generator 12 positioned externally). Another example of a current generator 12 is an implantable generator (IPG) (at least a portion of the current generator 12 positioned subcutaneously). It will be appreciated that the current generator 12 can include additional components to selectively configure the current waveform, such as an amplitude modulator (not shown).

The current generator 12 can generate, configure, and deliver a DC waveform to the subcutaneous electrode 14. In some instances, the generated DC can have an anodic polarity or a cathodic polarity, and an amplitude sufficient to cause the nerve conduction block via an electrical field greater than the block threshold and a ramp sufficient to block the onset response. As one example, the current generator 12 can be configured or programmed to generate a monophasic DC waveform. In other examples, the current generator 12 can be configured or programmed to generate a DC having a biphasic waveform, with one phase cathodic and one anodic. In this case, the altering DC can be delivered to the nerve in the first phase for a specific period of time, while a second phase having an opposite polarity can reduce or eliminate unwanted effects generated by the first phase. In some instances, a generated biphasic DC waveform can be a charge-balanced biphasic waveform that produces zero net charge. In other instances, a generated biphasic DC waveform can be applied as a substantially charge-balanced DC waveform that produces a small net charge.

The subcutaneous electrode 14 can receive the DC from the current generator 12 and deliver the DC to the neural structure to block conduction in the neural structure. The subcutaneous electrode 14 is implantable under the subject's skin. More specifically, the subcutaneous electrode 14 can be positioned between the subject's skin and the neural structure. Notably, the subcutaneous electrode 14 need not contact the neural structure. Instead, the subcutaneous electrode 14 is implantable under the skin to eliminate an effect of an impedance of the subject's skin on the delivery of the DC. The return electrode 16 can complete the circuit between the subcutaneous electrode 14 and the current generator 12 to return the DC to the current generator after application to the neural structure. The return electrode 16 can be located subcutaneously, but not immediately adjacent to the neural structure. However, in some instances, the return electrode 16 can be located at least partially externally.

The subcutaneous electrode 14 and the return electrode 16 can be placed in a configuration depending on the application of the DC nerve conduction block. Non-exhaustive example configurations 20-60 of the subcutaneous electrode 24 and the return electrode 26 with the external current generator 22 (which can output a current controlled DC waveform) are shown in FIGS. 2-6. In each of the example configurations 20-60, the subject's skin is illustrated as a dashed line 23. Additionally, the neural structure is illustrated as a nerve 25. The delivery of the DC is shown as lines with arrows between the current generator 22 and the subcutaneous electrode 24, between the subcutaneous electrode 24 and the return electrode 26, and between the return electrode 26 and the current generator 22.

Figure 2:
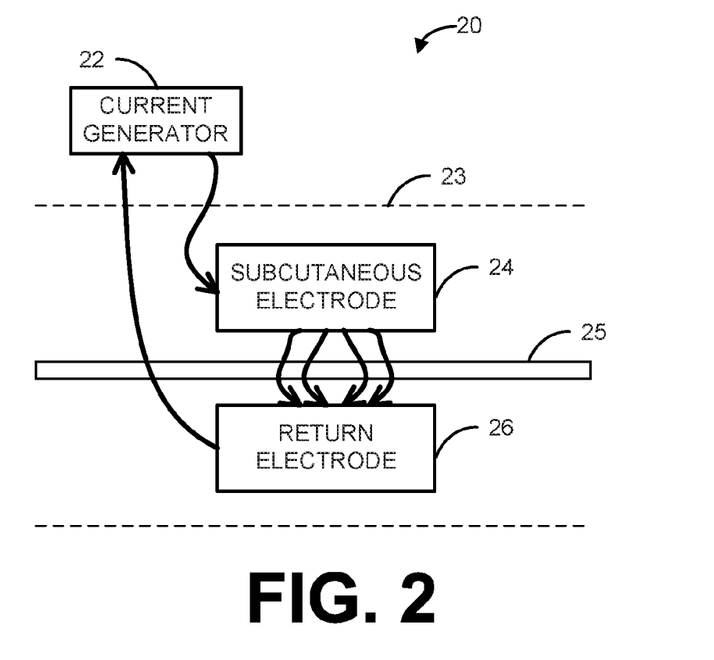
FIGS. 2-6 are schematic diagrams of different arrangements of subcutaneous electrodes that can be used by the system in FIG. 1.
Figure 3:
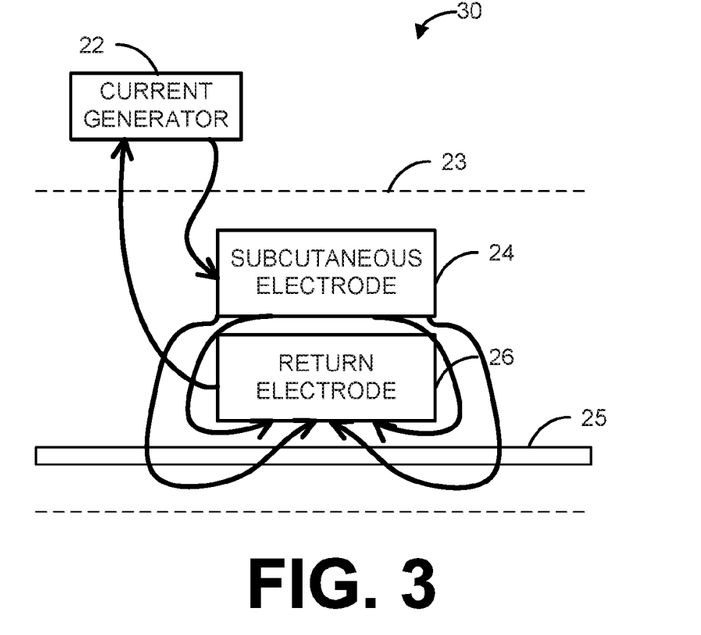
Figure 4:
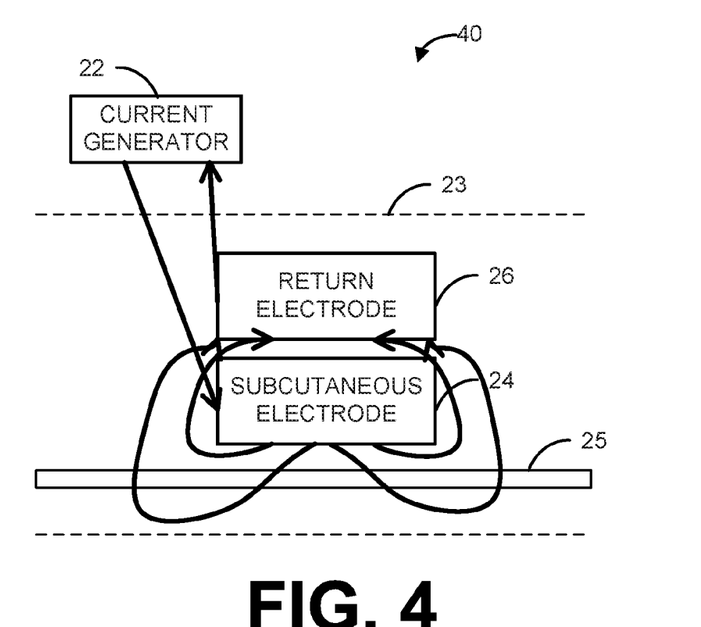
Figure 5:
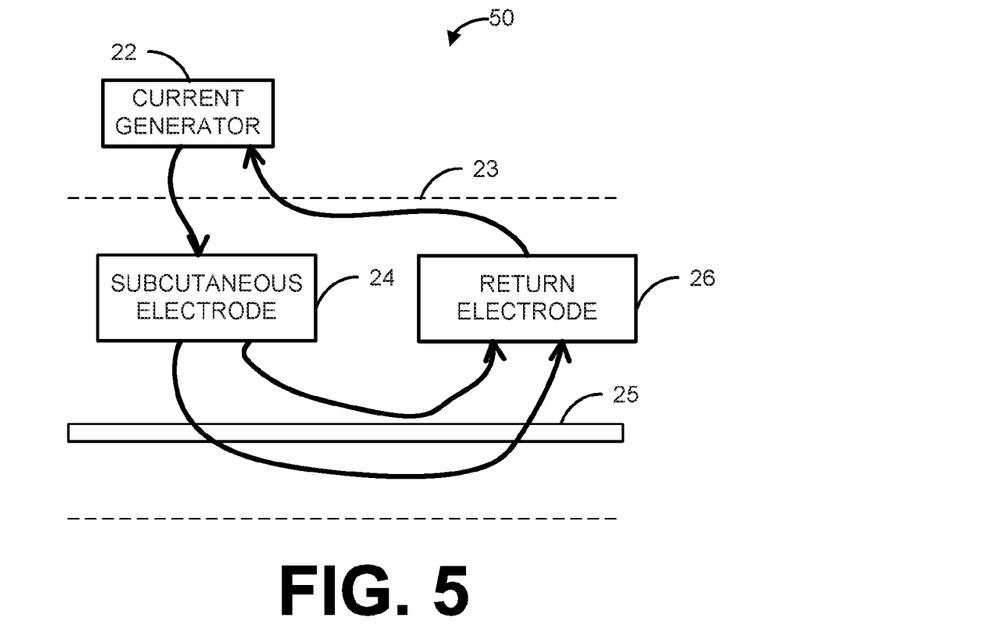
Figure 6:
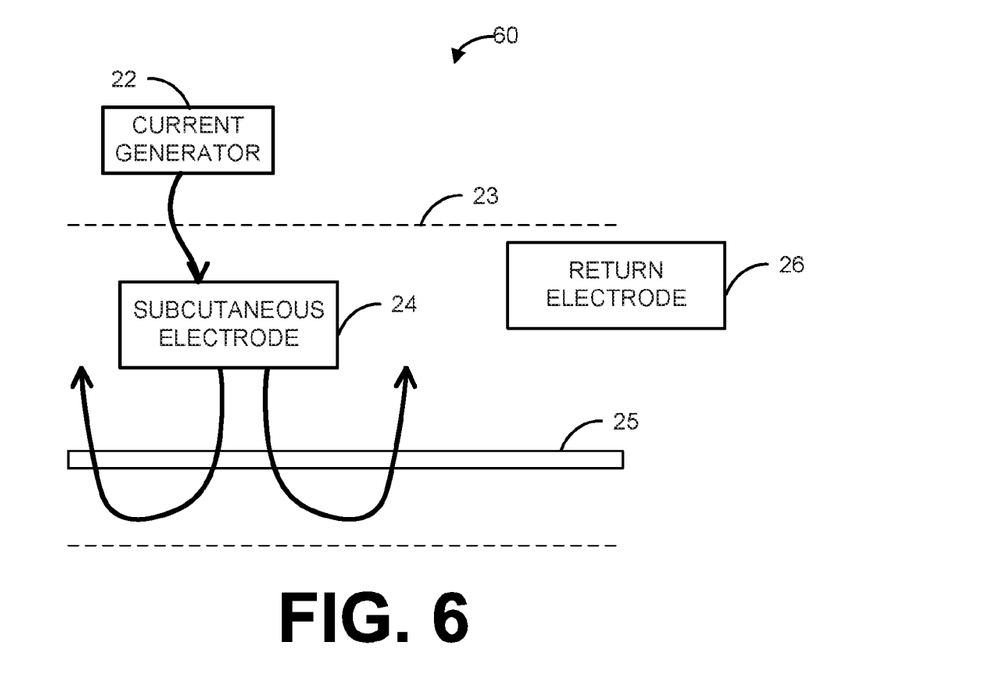

In FIG. 2, the subcutaneous electrode 24 and the return electrode 26 can be positioned across the nerve 25. In other words, the return electrode 26 is directly opposed to the subcutaneous electrode 24. In FIGS. 3 and 4, the subcutaneous electrode 24 and the return electrode 26 can be stacked near the nerve. The return electrode 26 is more proximal to the nerve than the subcutaneous electrode 24 in FIG. 3. FIG. 4 shows the reverse, where the subcutaneous electrode 24 is placed more proximal to the nerve than the return electrode 26. In FIG. 5, the subcutaneous electrode 22 and the return electrode 26 can be placed side by side near the nerve. In other words, the subcutaneous electrode 24 is next to the return electrode 26. In FIG. 6, the return electrode 26 can be placed remotely from the subcutaneous electrode 24. The subcutaneous electrode 24 is placed near the nerve, while the return electrode 26 is placed remotely in tissue within the subject's body, but not necessarily near the nerve.

Figure 7:
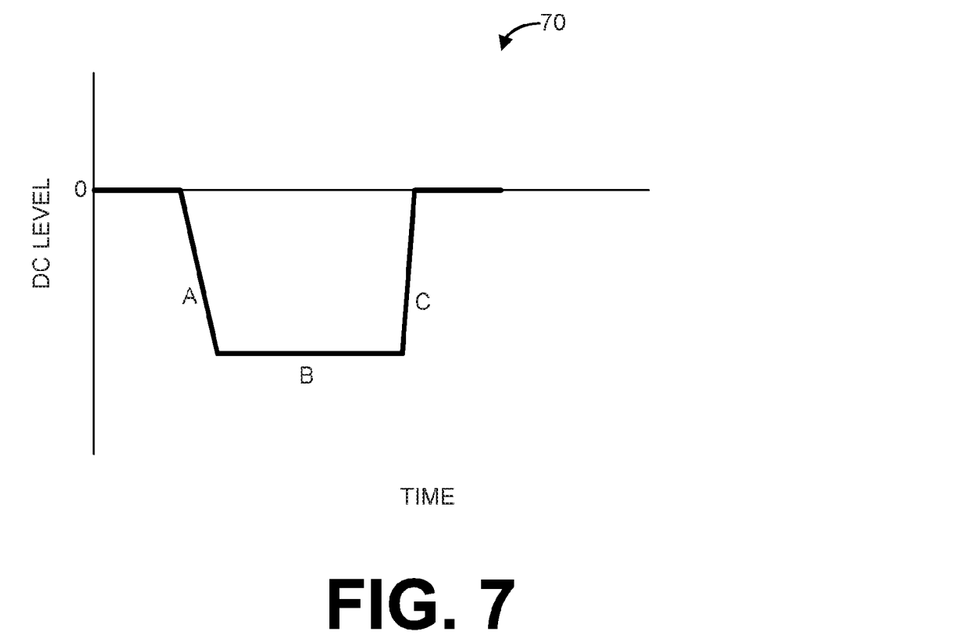
FIG. 7 is an illustration of an example DC waveform that can be used by the system in FIG. 1.

When arranged in the configurations 20-60, the subcutaneous electrode 24 can deliver a single-phase DC waveform (either cathodic or anodic polarity) without requiring a recharge phase. An example of such a monophasic waveform 70 is shown in FIG. 7. The waveform is ramped down (A) from 0 to the DC plateau to counteract the onset response. Then the waveform remains at the DC plateau (B) for a period of time sufficient to generate the electrical field that achieves the DC nerve conduction block. The DC plateau (B) generates an electrical field at least greater than the block threshold. The DC plateau then ramps back (C) to 0. This second ramp (C) may be unnecessary in some instances and need not be used. The single phase can repeat periodically with an on time (when the DC plateau and ramps are applied) and an off time (when the current is 0).

Figure 8:
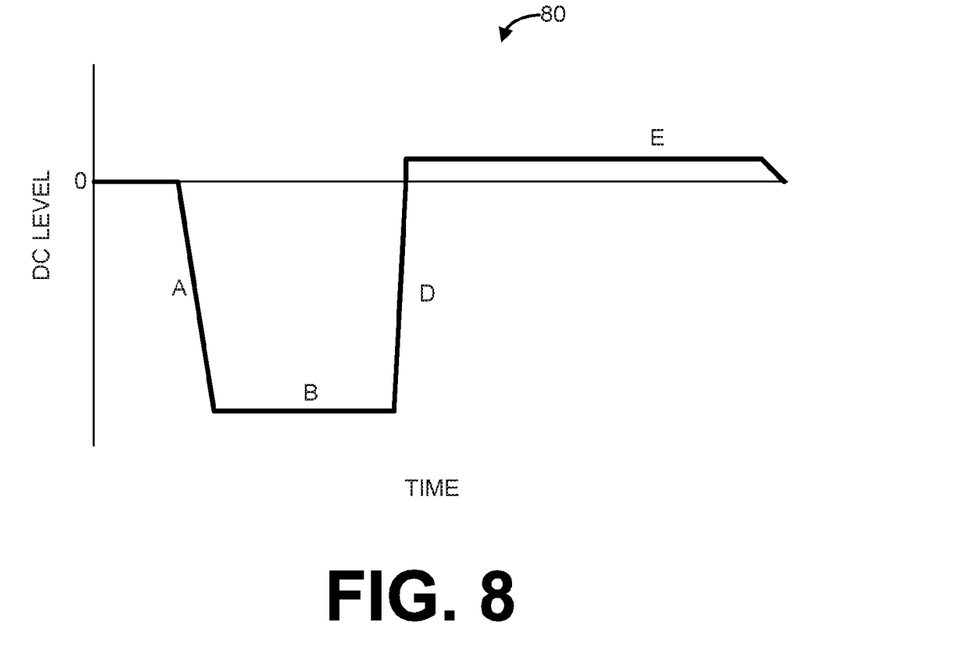
FIG. 8 is an illustration of an example charge balanced DC waveform that can be used by the system in FIG. 1.

However, even when arranged in configurations 20-60, it may be advantageous for the subcutaneous electrode 24 to deliver a balanced charge biphasic waveform 80, as shown in FIG. 8. The charge balanced biphasic waveform 80 can be used to prevent the accumulation of charge in the tissue. The first phase of the waveform is ramped down (A) from 0 to the DC plateau to counteract the onset response. Then the first phase of the waveform remains at the DC plateau (B) for a period of time sufficient to generate the electrical field that achieves the DC nerve conduction block. The DC plateau (B) generates an electrical field at least greater than the block threshold. The DC plateau then ramps back (D) past 0 to the DC plateau with the reverse polarity (E) of the second phase. The DC plateau with the reverse polarity (E) can have a lower DC value than the DC plateau. However, the DC plateau with the reverse polarity (E) can be longer in time to compensate for the lower amplitude. The biphasic waveform can repeat periodically.

IV. Methods

Another aspect of the present disclosure can include a method 90 (FIG. 9) for direct current (DC) nerve conduction block using an arrangement of subcutaneous electrodes. The method 90 can be executed using the system 10 shown in FIG. 1 and described above. The subcutaneous electrodes can be arranged, for example, in any one of the configurations as shown in FIGS. 2-6.

Figure 9:
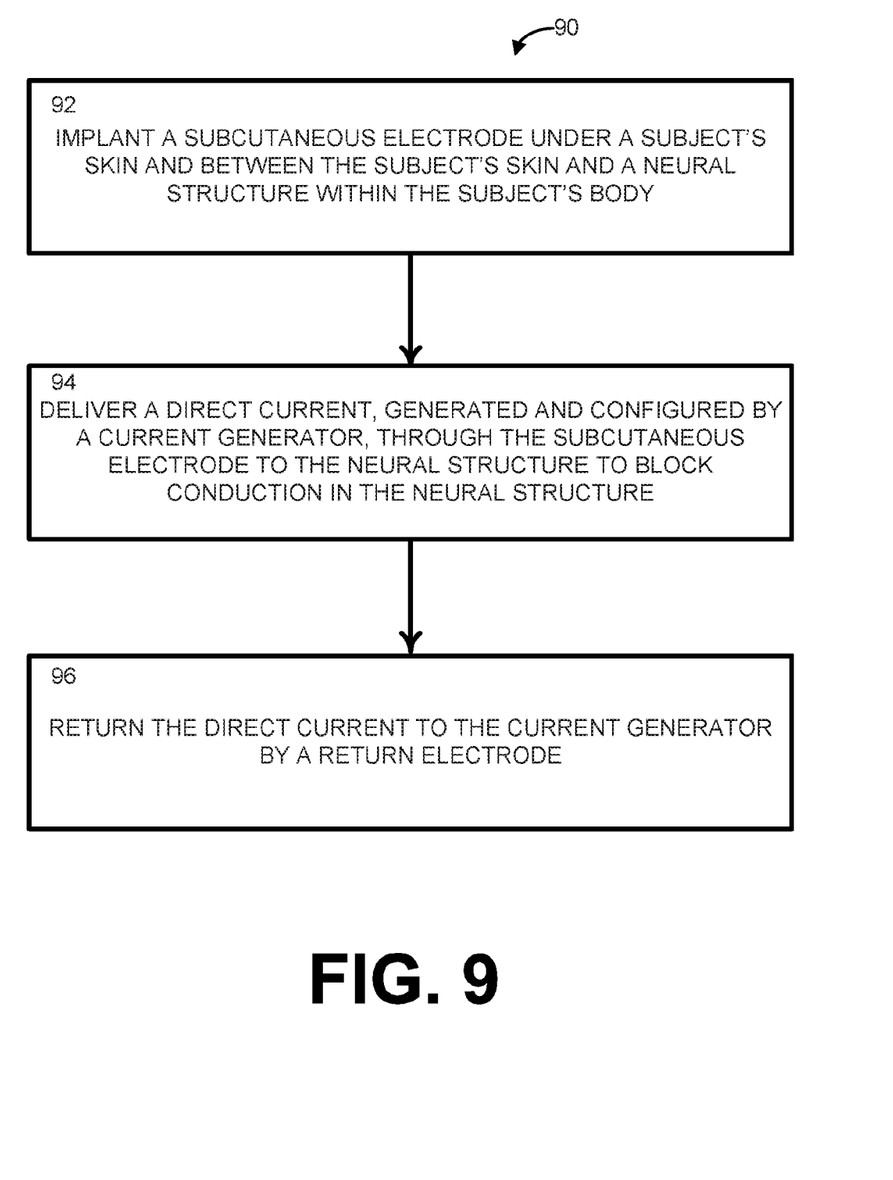
FIG. 9 is a process flow diagram illustrating a method for DC nerve conduction block using an arrangement of subcutaneous electrodes according to another aspect of the present disclosure.

The method 90 can generally include the steps of: implanting a subcutaneous electrode under a subject's skin and between the subject's skin and a neural structure within the subject's body (Step 92); delivering a DC, generated and configured by the current generator, through the subcutaneous electrode to the neural structure (Step 94); and returning the DC to the current generator by a return electrode (Step 96). The method 90 is illustrated as process flow diagrams with flowchart illustrations. For purposes of simplicity, the method 90 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 90.

At Step 92, a subcutaneous electrode (e.g., element 14 of FIG. 1) is implanted under a subject's skin and between the subject's skin and a neural structure within the subject's body. The subcutaneous electrode is coupled to a current generator (e.g., element 12 of FIG. 1) and placed in proximity to a neural structure without necessarily touching the neural structure. In some examples, the neural structure can be a peripheral nerve or neural fibers (e.g., motor, sensory, enteric, and/or autonomic) or a nerve or nervous tissue comprising the central nervous system (e.g., brain and/or spinal cord).

The current generator can generate and configure the DC to be applied to the neural structure. The DC can be configured for the specific applications, such as based on the block threshold of the target neural structure, with a certain ramp from 0 to the desired DC (examples of DCs that can be applied are shown in FIGS. 7 and 8). The DC can have an amplitude sufficient to alter transmission of action potentials in the target neural structure. For example, the DC can be anodic or cathodic and have an amplitude sufficient to generate an electric field that is able to alter transmission of action potentials in the target neural structure. In some instances, the DC can be applied as a biphasic waveform, with the second phase operable to reverse the charge delivered by the first phase. In other instances, the second phase can reverse less than 100% of the total charge delivered by a first phase of the biphasic waveform to reduce electrochemical reactions that are damaging to the nerve and/or the electrode. At Step 94, DC, which has been generated and configured by the current generator, can be delivered through the subcutaneous electrode to the neural structure to block conduction in the neural structure.

At Step 96, the DC can be returned to the current generator by a return electrode (e.g., element 16 of FIG. 1). As illustrated in FIGS. 2-6, the return electrode can be arranged across the neural structure from the subcutaneous electrode (FIG. 2), stacked near the neural structure from the subcutaneous electrode (FIGS. 3 and 4), arranged side-by-side with the subcutaneous electrode near the neural structure (FIG. 5), or arranged remote from the subcutaneous electrode (FIG. 6). It should be noted that in each of FIGS. 2-6, the return electrode is also subcutaneous under a subject's skin and between the subject's skin and a neural structure within the subject's body. However, the return electrode may, in some instances, be a surface electrode or other type of electrode external to the subject's body.

V. Examples

Direct current (DC) nerve conduction block is fast acting, reversible, onset free, and easy to modulate, making it ideal for a variety of applications in a patient's nervous system. Application of the DC nerve conduction block via subcutaneous electrodes provides a less invasive solution than traditional nerve cuff electrodes, while removing the skin to electrode impedance of skin surface electrodes. As an example, the impedance of subcutaneous electrodes can be less than 1 kilo-ohm, while the impedance of surface electrodes may be more than 1 kilo-ohm. Given an electrode of a similar size and material, the impedance can be at least 50% less when using a subcutaneous electrode compared to the surface electrode. This translates directly into the amount of charge required to achieve the DC nerve conduction block.

It will be appreciated that subcutaneous DC nerve conduction block can be applied to one or more neural structures related to the central nervous system, peripheral nervous system, autonomic nervous system, and enteric nervous system. However, described below are certain examples of some of the various medical conditions for which subcutaneous DC nerve conduction block can be used. The following examples are for the purpose of illustration only is not intended to limit the scope of the appended claims.

Motor System

In the motor system, spasticity is a debilitating condition that is a result of many different neurological conditions. A few examples of such neurological conditions include cerebral palsy, multiple sclerosis, spinal cord injury and stroke. In each example, the onset of spasticity results in many impairments and limitations including, but not limited to, gait disorders, fatigue, restricted range of movement, abnormal limb postures, quality of life issues, problems with activities of daily living, and/or pain, all of which impact the patient's quality of life. In addition to the quality of life impact of spasticity, the economic burden of any neurological condition increases significantly at the onset of spasticity. For stroke, it has been demonstrated that spasticity causes a four-fold increase in the direct costs associated with treating stroke patients. Direct current nerve conduction block can be applied subcutaneously and modulated to provide a solution that can minimize spasticity while maintaining muscle tone allowing for previously unattainable functional improvements.

Sensory System

In the sensory system, chronic neuropathic pain would be an ideal target for subcutaneous DC nerve conduction block. Neuropathic pain follows trauma or disease affecting the peripheral or central nervous system. Examples of such trauma can include physical trauma, spinal cord injury, while examples of such disease can be a side effect of chemotherapy, radiation, or surgery.

With some peripheral neuropathic pain, the source of the pain is localized at a neuroma. As is common with amputations, when a peripheral nerve is damaged, the peripheral nerve tries to regenerate itself towards the distal target. If the distal target is unavailable, axon sprouts grow into the surrounding scar tissue forming a neuroma, which can cause chronic pain and hypersensitivity. A neuroma is particularly well suited to subcutaneous DC nerve conduction block given the local nature of the condition. Also, with subcutaneous DC nerve conduction block, the subcutaneous electrode can easily be removed and placed in a different location, making the subcutaneous electrode desirable in the event that the neuroma changes in a way that lessens the effect of the nerve block.

Autonomic System

In the autonomic system, the properties of subcutaneous DC nerve conduction block provide a unique opportunity for modulation of neural activity. The autonomic nervous system frequently operates around a baseline of neural activity, which is modulated up or down to produce the desired physiological effects. For example, blood pressure is maintained through tonic activity in the autonomic nervous system. It would be extremely beneficial to not only be able to enhance neural activity, but also to inhibit neural activity in a graded/modulated manner. Direct current can be modulated to affect a sub-population of axons to achieve a graded response. In the autonomic system, the onset response is particularly confounding since the effect is prolonged due to the dynamics of the system. The ability to produce an onset free nerve block is absolutely critical to provide an effect solution to autonomic diseases, and the subcutaneous nature of the block leads to greater use of the block throughout the medical community.

Regional Applications

Some regional applications are well suited to a subcutaneous direct current intervention. As an example, damage to the occipital nerve can result in chronic headache symptoms. Pharmacological nerve blocks, which are often used to treat this condition, could easily be replaced with a minimally invasive subcutaneous direct current nerve block which would provide a longer term relief. As another example, the pudendal nerve has successfully been blocked using KHFAC and nerve cuff electrodes for bladder control. Both of these methods could be enhanced by less invasive solution. Also, the DC would be capable of providing smooth transitions between partial and complete block which could further improve the functionality of the application.

From the above description, those skilled in the art will perceive improvements, changes and modifications. Such improvements, changes and modifications are within the skill of one in the art and are intended to be covered by the appended claims.

The following is claimed:

1. A method comprising:
   implanting a subcutaneous electrode under a subject's skin and between the subject's skin and a neural structure within the subject's body, wherein the subcutaneous electrode is connected to an external current generator via a percutaneous wire that extends through the subject's skin;
   delivering a waveform, comprising a ramp to a direct current (DC) plateau, the DC plateau having an amplitude sufficient to alter transmission of action potentials in the neural structure, and a ramp down from the DC plateau, configured by the current generator, through the subcutaneous electrode to block conduction in the neural structure in a reversible manner to treat a neurological condition, wherein the subcutaneous electrode eliminates an effect of an impedance of the subject's skin on the waveform, wherein the waveform does not trigger an onset response upon application; and
   returning the waveform to the external current generator by a return electrode.

2. The method of claim 1, wherein the neural structure comprises at least one of tissue related to the central nervous system, peripheral nervous system, autonomic nervous system, and enteric nervous system.

3. The method of claim 1, further comprising placing the return electrode on an opposite side of the neural structure to the subcutaneous electrode.

4. The method of claim 1, further comprising stacking the return electrode and the subcutaneous electrode between the subject's skin and the neural structure.

5. The method of claim 1, further comprising placing the return electrode side-by-side with the subcutaneous electrode between the subject's skin and the neural structure.

6. The method of claim 1, further comprising placing the return electrode remote to the subcutaneous electrode inside the subject's body.

7. The method of claim 1, wherein the waveform comprises a single phase without a recharge phase.

8. The method of claim 1, wherein the block of conduction at least one of reduces spasticity, reduces neuropathic pain, reduces chronic headache symptoms, allows for bladder control, or modulates autonomic activity.

9. The method of claim 1, wherein the block of conduction in the neural structures comprises a partial block of conduction in the nerve fibers within the nerve.

10. A system comprising:
an external current generator to generate a waveform including a ramp to a DC plateau, the DC plateau having an amplitude sufficient to alter transmission of action potentials in the neural structure, and a ramp down from the DC plateau;
a subcutaneous electrode, connected to the external current generator via a percutaneous wire that is configured to extend through the subject's skin, to deliver the DC to block conduction in one or more neural structures in a subject's body in a reversible manner to treat a neurological condition, wherein the subcutaneous electrode is implantable under the subject's skin and between the subject's skin and the one or more neural structure within the subject's body to eliminate an effect of an impedance of the subject's skin wherein the waveform does not trigger an onset response upon application; and
a return electrode, coupled to the external current generator.

11. The system of claim 10, wherein the return electrode is configured to be placed on an opposite side of the one or more neural structures to the subcutaneous electrode.

12. The system of claim 10, wherein the return electrode is configured to be stacked with the subcutaneous electrode under the subject's skin and between the subject's skin and the one or more neural structures.

13. The system of claim 10, wherein the return electrode is configured to be side-by-side with the subcutaneous electrode under the subject's skin and between the subject's skin and the one or more neural structures.

14. The system of claim 10, wherein the return electrode is configured to be placed remote to the subcutaneous electrode inside the subject's body.

* * * * *

UNITED STATES PATENT AND TRADEMARK OFFICE
CERTIFICATE OF CORRECTION

| | | |
|---|---|---|
| PATENT NO. | : 11,628,299 B2 | Page 1 of 1 |
| APPLICATION NO. | : 16/341511 | |
| DATED | : April 18, 2023 | |
| INVENTOR(S) | : Tina Vrabec et al. | |

It is certified that error appears in the above-identified patent and that said Letters Patent is hereby corrected as shown below:

In the Specification

Column 1, Line 11 before the TECHNICAL FIELD heading please insert the following paragraph:
--GOVERNMENT FUNDING
This invention was made with government support under NS074149 awarded by the National Institutes of Health. The government has certain rights in the invention.--

Signed and Sealed this
Third Day of June, 2025

Coke Morgan Stewart
*Acting Director of the United States Patent and Trademark Office*